United States Patent [19]
Martin

[11] Patent Number: 6,132,464
[45] Date of Patent: Oct. 17, 2000

[54] VERTEBRAL JOINT FACETS PROSTHESES

[75] Inventor: Jean-Raymond Martin, Tournefeuille, France

[73] Assignee: Paulette Fairant, Tournefeuille, France

[21] Appl. No.: 08/773,655

[22] PCT Filed: Jun. 16, 1995

[86] PCT No.: PCT/FR95/00802
§ 371 Date: Dec. 24, 1996
§ 102(e) Date: Dec. 24, 1996

[87] PCT Pub. No.: WO96/00049
PCT Pub. Date: Jan. 4, 1996

[30] Foreign Application Priority Data

Jun. 24, 1994 [FR] France ................................. 94 07774

[51] Int. Cl.[7] .................................................. A61F 2/44
[52] U.S. Cl. .............................. 623/17; 623/16; 606/61
[58] Field of Search ................................. 623/16, 17, 18; 606/60, 61, 70–73

[56] References Cited

U.S. PATENT DOCUMENTS

| | | | |
|---|---|---|---|
| 4,936,848 | 6/1990 | Bagby | 623/17 |
| 5,011,484 | 4/1991 | Breard | 623/17 |
| 5,074,864 | 12/1991 | Cozad et al. | 606/61 |
| 5,127,912 | 7/1992 | Ray . | |
| 5,306,275 | 4/1994 | Bryan | 606/61 |
| 5,366,455 | 11/1994 | Dove et al. | 606/61 |
| 5,391,168 | 2/1995 | Sanders et al. | 606/61 |
| 5,415,661 | 5/1995 | Holmes | 623/17 |
| 5,458,641 | 10/1995 | Ramirez Jimenez | 606/61 |
| 5,496,318 | 3/1996 | Howland et al. | 606/61 |
| 5,507,745 | 4/1996 | Logroscino et al. | 606/61 |
| 5,571,191 | 11/1996 | Fitz | 606/61 |
| 5,584,832 | 12/1996 | Schlapfer | 606/61 |
| 5,603,713 | 2/1997 | Aust et al. | 606/61 |
| 5,609,634 | 3/1997 | Voydeville | 606/61 |

*Primary Examiner*—Mickey Yu
*Assistant Examiner*—Tram A. Nguyen
*Attorney, Agent, or Firm*—Harold H. Dutton, Jr.

[57] ABSTRACT

A device for replacing all or part of the posterior vertebral articular process (3, 13), engaging a support (7) and members for anchoring same to the vertebra, wherein each complete (5) or partial (1, 11), upper (1, 5) and/or lower (11) prosthesis mimics the anatomical shape of the posterior vertebral articular process and comprises artificial sliding surfaces (2, 12) facing one another between at least two adjacent vertebrae while adapting to the physiological orientation thereof, and the anchoring members comprise a support (7) with a convex surface matching and engaging at least one portion of the concave surface of the posterior arch of the vertebra on at least one side of the spinous process (9), and rigidly connect at least one separate portion of the support (7), to a corresponding separate portion of the vertebra.

19 Claims, 8 Drawing Sheets

VERTEBRAL JOINT FACETS PROSTHESES

This invention relates to devices for replacement of posterior vertebral facets articular surfaces affected by varying degrees of degeneration and/or destruction, and elements for anchoring these prostheses on the vertebrae. These prosthetic elements are made of a solid casting of support plate-artificial articular blade, fixed on the corresponding vertebra by anchoring means onto the pedicles and/or transverse processes and/or spinous process.

With respect to vertebral articular surface degeneration, arthrosis of the joint facets is found which shows a reduced thickness of cartilage and may advance to entire disappearance thereof. Furthermore, surrounding the degenerated articular surfaces, there is bony formation able to give neurological compressions inside either foramenae or spinal canal. These facts induce lower back and nerve roots pain which involve a large part of the population.

As often as not, a degenerative disease is found which involves articular surfaces only, but may also have a more invasive pathology including traumatic, infectious, tumorous or dysmorphic (spondylolisthesis, for example) effecting the destruction of all or part of the articular process.

It is essential to reduce and/or to remove frictions on degenerated articular surfaces: until now, this aim has been achieved either by fixing all motions between concerned vertebrae with spinal arthrodesis or fusion more or less associated with an osteosynthesis (Harrington, Cotrel-Dubousset, TSRH, New Orleans, etc.) or by reducing these frictions with a spinal ligamentoplasty (Graaf, Senegas, Lemaire, etc.).

The locking of vertebral motions by spinal arthrodesis or ligamentoplasty induces, beyond a spinal stiffness, an increased strength on the joint facets of the adjacent vertebrae above and below the fusion, usually sustained by the considered intervertebral space and therefore an increase of degeneration of these joint facets.

With regard to discal prostheses, they provide a "space" between two vertebral bodies while preserving some motion. They solve the aging intervertebral disc problem but don't function for reducing the strength on posterior joint facets of which the motions and the frictions are maintained.

Therefor the invention aims at overcoming disadvantages of all known devices by providing a new device which enables replacement of degenerated articular surfaces with articular prostheses. These prostheses preserve vertebral motion while cancelling "bone-cartilage" frictions of degenerated surfaces and therefore pain and/or osteophytic induction with nerve root compressions in foramenae.

Further, the invention relates to prosthetic devices for treatment of the articular surface and to larger prosthetic elements for total replacement of bony process and its articular surface. The invention aims at preserving the spinal stability by the intervertebral "hooking" of the process prosthetic devices between them, as made by the natural vertebral processes, and at preserving the potential of functional motion without damaging the spinal muscles-ligaments system.

According to the invention, these prosthetic elements, built with biocompatible materials such as metallic alloy (stainless steel, titanium, or other) and/or composite material have a first "articular" surface which is matched with the similar surface of the adjacent vertebra for sliding between themselves with a minimal friction, and second opposite "bony" porous surface, with scattered protruding points, coated or not with hydroxy-apatite, for resting on the remaining bone of the vertebral articular process. Thus according to the invention, these prosthetic elements replace at least the articular surfaces of one intervertebral space according to inferior joint facets of the superior vertebra and to superior joint facets of the inferior vertebra. If necessary, the prostheses may be unilateral but more often than not, and preferably, bilateral.

According to the invention, if the remaining bone of the articular process is too weak, the prosthesis replaces the total process and therefore always has a sliding "articular" surface; but the usually "bony" opposite surface is replaced by a thickening of the prosthesis, so as to replace totally the natural articular process of which it mimics all anatomic features according to the shape, the volume and the orientation, with a smooth and slightly convex face to eradicate all risks for spinal cord or nerve roots present medially and in the front.

Considering on one hand the small quantity of bone of the vertebral posterior arch which includes the articular process and on the other hand the "cancellous" brittle quality of this bone, the problem of first importance is the anchoring of these artificial joint facets prostheses. In fact the anchorage must realize a fautless stability of these articular prostheses which will sustain strength induced by intervertebral motions, since they aim to preserve these intervertebral motions.

Therefore the invention seeks to eradicate these anchorage problems due to the weak bony capital of each joint facet by providing an anchoring device for vertebral joint facet prosthesis, including at least one support carrying means for linking the prosthesis to this support and means for anchoring the support with respect to the vertebra, wherein the support has a convex face which fits and bears with contact against at least one portion of the concave surface of the posterior arch of the vertebra, on at least one side of the spinous process, and wherein the anchoring means rigidly links at least one distinct portion of the support with at least one distinct corresponding part of the vertebra.

According to another feature of the invention, the device has at least one support, the convex face of which extends facing either the spinous process and/or one transverse process and/or one pedicle of the vertebra, and means for anchoring the support, respectively, onto either the spinous process and/or one transverse process and/or one pedicle of the vertebra. The intrapedicular screw, when not used alone, is not essential and then may eventually be replaced by one usual short screw through the posterior cortex and stopping in the cancellous bone facing the pedicle: this prevents any risk of neurological injury.

According to the invention, each support is formed by a plate carrying coupling means and covering a portion of the concave surface of the posterior arch of the vertebra on at least one side of the spinous process.

A device according to the invention may have two supports, one on each side of the spinous process of the vertebra, or one single support extending on only one side, or on both sides of the spinous process. Advantageously and in accordance with the invention, the two supports are, together, linked with the same spinous process by common anchoring means. The spinous process, the cortical part of which is left completely unaffected, is thus buttressed and therefore supports and unites the two bilateral supports. The two sides of the posterior vertebral arch are used for an anchorage, even for a unilateral prosthesis.

According to the invention, the means for anchoring each support has at least one hook which is articulated on the support about a spindle, the hook carrying a clamping screw fitted into a threaded hole in the hook, the screw being supported either directly or indirectly on the support or on another hook, so as to cause the hook to pivot about its spindle in the direction in which the free end of the hook is clamped onto the corresponding part of the vertebra. Advantageously and in accordance with the invention, the anchoring means has at least one clamping claw formed by two hooks which are articulated on the same spindle or on parallel spindles and the mutually facing free ends of which are clamped towards one another.

According to the invention, the means for anchoring each support includes at least one flange for clamping one end of the support onto a vertebral process, and particularly onto a spinous and/or a transverse process.

Moreover, according to the invention, the convex face of the support is formed by a porous metal and is advantageously coated with a layer of hydroxy-apatite. This bony surface has points scattered thereon, circular or polyhedral, from 1 to 2 mm height, in order to insure better planting and anchorage of the support on the cortical bone of the posterior vertebral arch.

Also the invention relates to an anchoring device having, in combination, all or some of the characteristics mentioned above or below.

According to the invention, the means for linking the prosthesis to its support is made by the sessile base of this prosthesis: that is to say this base widens out progressively from the prosthetic blade to the support plate, being wider and thicker than this prosthetic blade that it sustains. This base is in superior or inferior position and thus induces the link with vertebral anchorage means.

According to the invention, the prosthetic element of the vertebral articular process has:

at least one posterior support plate (7) fitted to be rigidly anchored to a vertebra by matching with at least a part of posterior vertebral arch, at least one prosthetic blade (1, 11, 5) of joint facet, including or not the total replacement of the vertebral posterior articular process (3, 13), on which it is supported on, and wherein each prosthetic blade (1, 11, 5) is borne by one support plate (7), extends from support plate (7) to natural position of joint facet which it replaces and has an artificial articular surface (2, 12) from which the shapes, the position and the orientation correspond to that natural joint facet (3, 13) which it replaces.

According to the invention, the prosthetic element has at least one support plate (7) which bears the superior prosthetic blade (1) with one articular surface (2), either flat or concave, directed to the back suitable for replacing one superior joint facet, and/or an inferior prosthetic blade (11) with one articular flat or convex surface (12) directed to the front, for replacing an inferior joint facet.

According to another aspect of the invention, the prosthetic element has at least one prosthetic blade (1, 11) adapted to be in contact with a residual part of the articular process, this prosthetic blade having a face opposite to an articular surface (2, 12) and facing a residual part of corresponding articular process (3, 13).

According to another feature of the invention, the prosthetic element has at least one prosthetic blade (5) for total replacement of one articular process (3, 13), this prosthetic blade (5) having a tuberous shape with artificial articular surface (2, 12), a bowed bump to limit posteriorly and laterally the spinal canal and posteriorly the foramen, as made by the natural articular process which it replaces.

According to still another feature of the invention, the prosthetic device has each prosthetic blade (1, 11, 5) linked to one support plate (7) with a sessile base (6, 16), the total prosthetic blade (1, 11, 5), support plate (7) and sessile base (6, 16) being constructed of a single, stiff, biocompatible material piece.

According to a further feature of the invention, the prosthetic device has each support plate (7) with a convex face which is built to fit and to bear in contact against the concave surface of a posterior vertebral arch, and wherein each support plate (7) is a thin plate built to prevent trouble with the adjacent soft tissues, in particular adjacent muscles and ligaments.

According to the invention, the prosthetic element has, on each side of spinous process (9) where one support plate (7) is provided, a stiff anchorage means for the support plate, (7) fitted to anchor this support plate (7) against the posterior arch of the vertebra:

either in connection with the pedicle (10) of the facing posterior arch, or in connection with the pedicle (10) and on a vertebral transverse process (8) or spinous process (9), or on a transverse process (8) and on the spinous process (9), or on a transverse process (8) on the spinous process (9), and in connection with pedicle (10) of the facing posterior arch.

According to the invention, the prosthetic element has one unilateral support plate (7) extending on one only side of vertebral spinous process (9).

Further according to the invention, the prosthetic element has one bilateral support plate (7) extending on both sides of vertebral spinous process (9).

According to another aspect of the invention, the prosthetic element has two support plates (7), one on each side of vertebral spinous process (9).

According to still another aspect of the invention, the prosthetic element has two support plates (7) which extend facing the spinous process (9) and anchor onto it by common anchorage means (21, 22).

In addition, according to the invention, the prosthetic element has stiff anchorage means for a support plate (7) on a transverse process (8) which has at least one hook (28) and/or at least one claw and/or at least one clamping collar (39) for support plate (7) which extends facing this transverse process (8).

According to another aspect of the invention, the anchoring means of the prosthetic element for the support plate (7) on the transverse process (8) has at least one hook (28, 34, 35) movable and articulated on the support plate (7) about one spindle (30, 36, 37), the movable hook (28, 34, 35) carrying a clamping screw (32, 42, 43), fitted into a threaded hole in the hook (28, 34, 35), this screw being supported either directly or indirectly on the support plate (7) or on another hook, so as to cause the hook (28, 34, 35) to pivot about its spindle (30, 36, 37) in the direction in which its free end is clamped onto the corresponding part of the vertebra.

The means for anchoring the prosthetic element has at least one clamping claw formed by two hooks (34, 35) having mutually facing free ends which are clamped towards one another.

The prosthetic element includes means for stiff anchoring of one support plate (7) onto a spinous process (9) and having at least one collar (21) and/or at least one flange (22) for clamping the support plate (7) which extends facing this said spinous process (9).

Each support plate (7) of the prosthetic element carries in addition means (49) for coupling one spinal instrumentation.

The bony support surface of each prosthetic blade (1, 11, 5) and/or of each support plate (7) is formed by porous metal with scattered raised points.

The bony support surface of each prosthetic blade (1, 11, 5) and/or of each support plate (7) is coated with a layer of hydroxy-apatite.

The vertebral articular prosthesis has one superior prosthetic element anchored onto the superior vertebra of the joint to be fitted, this superior prosthetic element including one inferior prosthetic blade (11) with one artificial inferior articular surface (12) and one inferior prosthetic element anchored onto the inferior vertebra of the joint to be fitted, this prosthetic element including one superior prosthetic blade (1) with one artificial articular surface (2), these said superior and inferior artificial articular surfaces having interconnected shapes matched to effect a joint between two vertebrae.

The invention also relates to a prosthesis for vertebral posterior joint facets including, in combination, all or some of the characteristics mentioned above or below.

Others characteristics, aims and advantages of the invention will emerge from the detailed description which follows with reference to the attached drawings in which.

Figure 1:
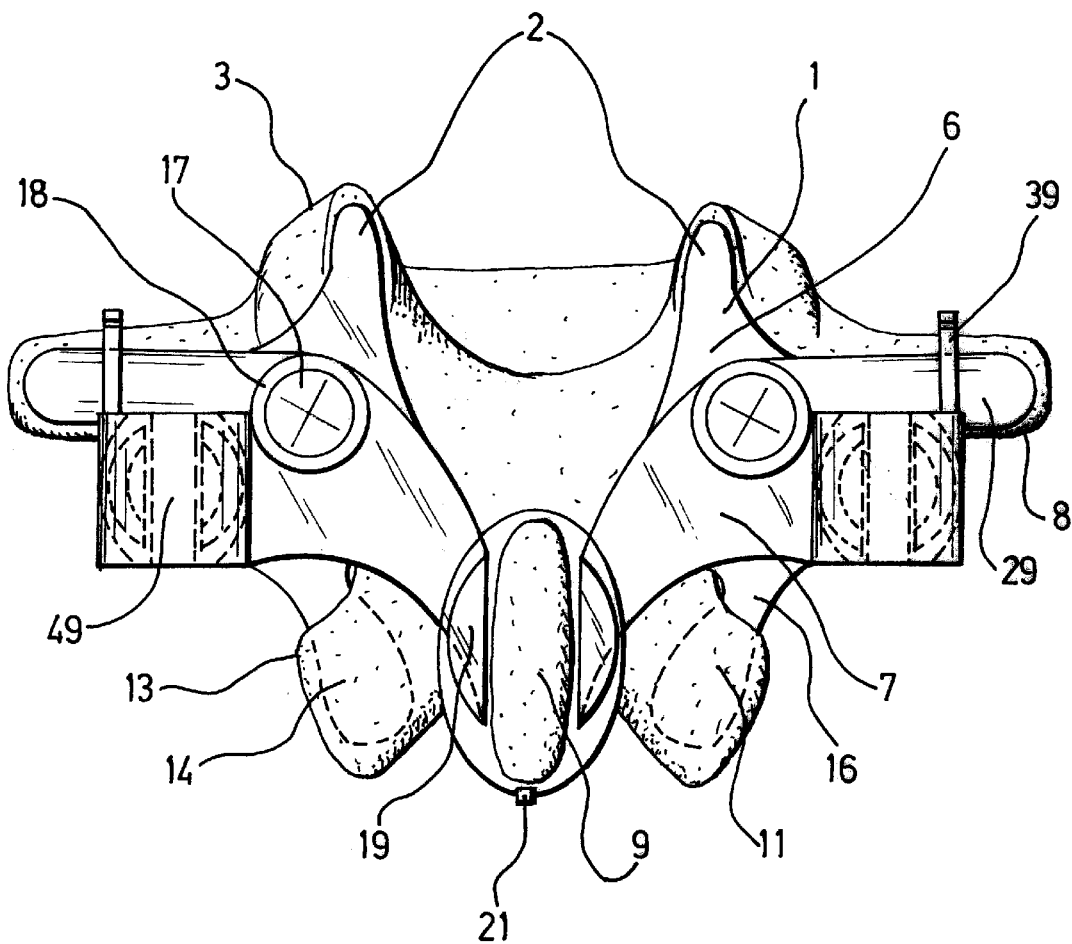
FIG. 1 is a diagrammatic rear view of an implanted vertebral prosthesis and effecting replacement bilaterally of the articular surfaces of the superior and inferior vertebral processes and showing possible connection with insertion of dynamic implanted vertebral orthosis fitted with anchoring devices according to the invention.
Figure 2:
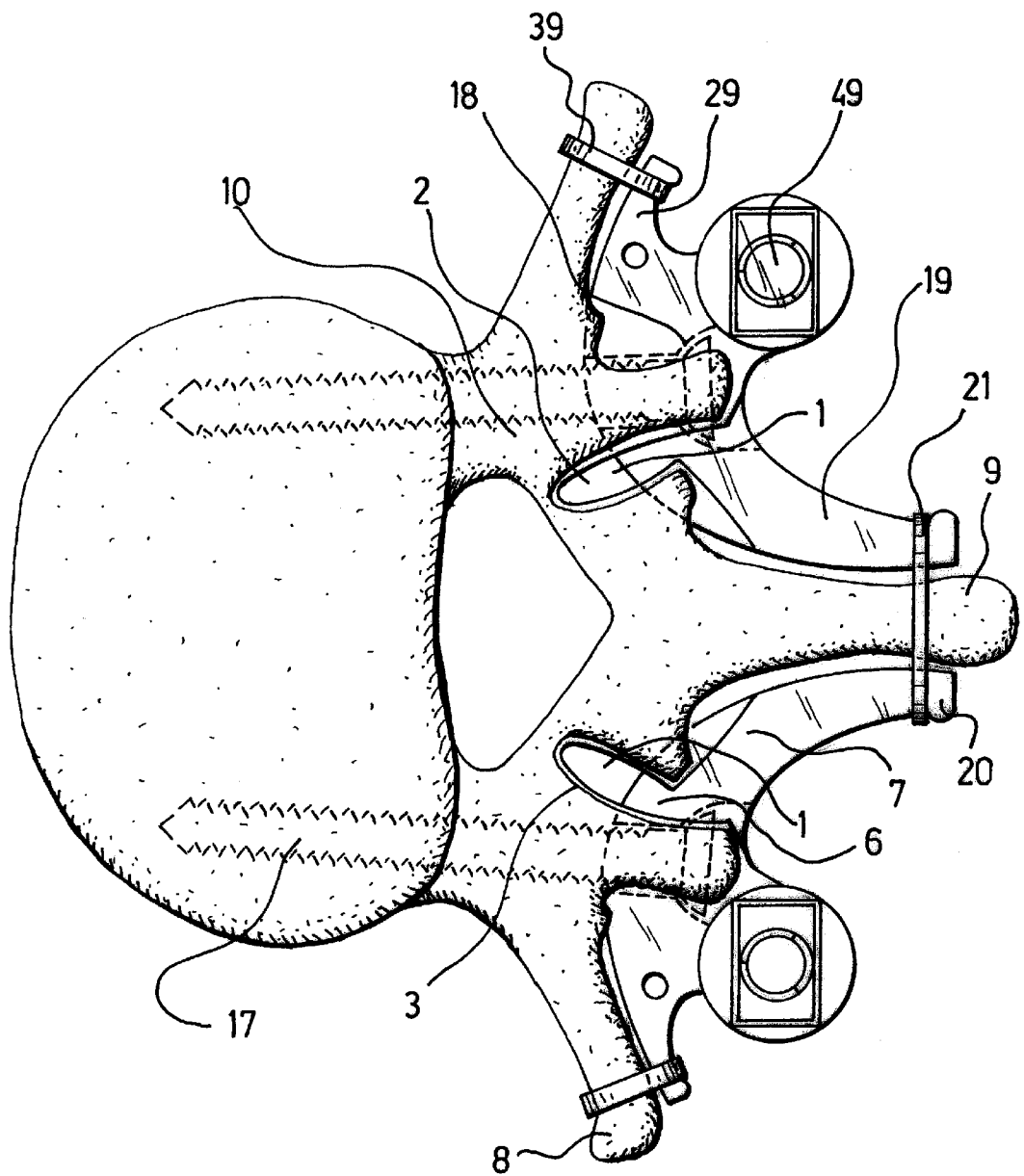
FIG. 2 is a diagrammatic view, in section through one horizontal plane of FIG. 1, showing the superior prostheses and their means for anchoring onto three points, i.e. pedicles, and transverse and spinous processes, carrying association into effect with one dynamic implanted vertebral orthosis.
Figure 3:
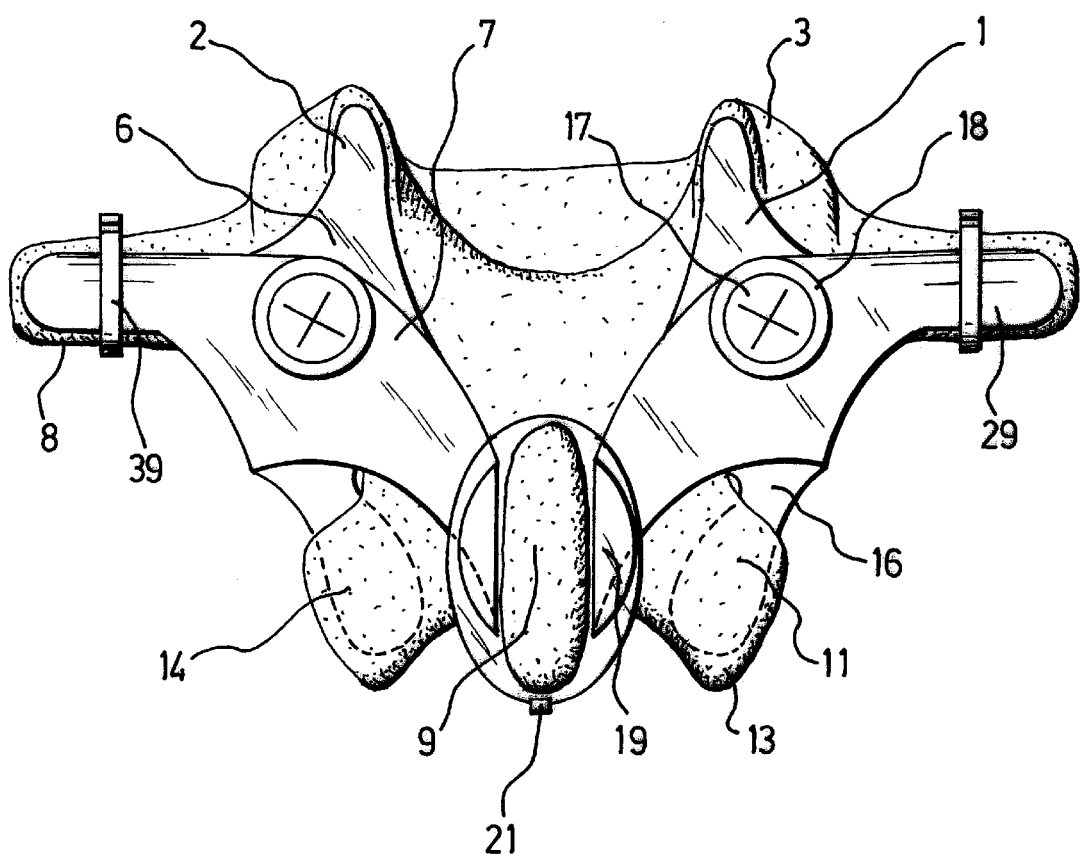
FIG. 3 is a diagrammatic rear view of one vertebral prosthesis implanted in a singular way and anchored onto the three usual anchoring points.

According to the invention, the blade 1 of the superior facet prosthesis has the same direction as the replaced joint. At the lumbar level, it is in a vertical and oblique plane with respect to the frontal and/or sagittal plane. Its surface 2 is posteriorly and medially directed. The approximately 45° angle at the lumbar level is variable with respect to the considered lumbar level. At the thoracic and cervical level it is directed more frontally and obliquely with respect to the horizontal plane. Then its surface 2 is directed posteriorly and above.

According to the invention, the prosthesis shape of the blade 1 is oval with a vertical major axis. Its surface 2 is usually flat but may be slightly concave (in accordance with the slightly convex surface 12 of the blade 11 of the prosthesis of the inferior articular process 13) to allow movement with some degree of rotation according to the considered vertebral level.

The blade 1 of the prosthesis, according to the invention, replaces the degenerated cartilage and therefore bears in contact against the remaining bone of the articular process 3. Its variable thickness, usually from 2 to 3 mm, may be larger if the required strength requires, and its non articular porous face may be coated with hydroxy-apatite for better anchoring and inclusion to the remaining bone.

In the event the fragility or lack of remaining bone justifies the total replacement of the articular process 3, the prosthetic blade is thickened to bear by itself all the needed strength and mimics the anatomical shape of the total considered articular process 13: its articular surface 2 remains the same as that used for partial replacement when the opposite face 5 is made by full material effecting one smooth convex face 5 which is the lateral and posterior limit of the spinal canal, and posterior limit of foramen.

According to the invention, the sliding surface 2 of this blade 1 of the prosthesis is coated with a biocompatible material with a high sliding rate (or low friction rate) as, and in no limiting way, stainless steel, titanium, ceramica, high molecular weight polyethylene or composite material. It will articulate with the surface 12 (with identical or different material) of the blade 11 of the inferior articular prosthesis of the superior vertebra. Its sizes correspond to that replaced articular surface and even may be reduced by 1 or 2 mm in the front to increase the frontal posterior foramen diameter and then to prevent any nerve roots compressions.

The link of the blade 1 of the prosthesis with its anchoring means is made with progressive widening of its base 6 which realizes one solid casting with its support 7. This sessile base 6 is convex and porous on its posterior face to apply on and to bear with contact against the posterior vertebral bone on which it rests. The support 7 is applied on the posterior face of the posterior vertebral arch, in matching its shapes: this support plate 7 is anchored onto the bone by at least one of its anchoring means on the transverse 8 or spinous 9 processes and/or pedicles 10.

If the blade 1 of this superior prosthesis is located on the inferior vertebra of the planned assembly, it stays alone on this vertebra when using, according to needs, one or many planned anchoring means. In the event the blade 1 of this superior prosthesis is fitted on one "intermediate" vertebra of the assembly, then it joins with the blade 11 of the inferior prosthesis with which it effects one cast solid with the support which thus realizes the same vertebral anchorage for the two prosthetic blades 1 and 11.

The blade 11 of the inferior articular process prosthesis 13, according to the invention, has the same direction as the replaced articular surface, that is to say it is in one vertical and oblique plane according to frontal and/or sagittal plane. The angle, about 45°, at the lumbar level, is variable in respect with the considered vertebral level and stays strictly parallel to that of the blade 1 of the superior articular process 3 prosthesis of the inferior vertebra on which it matches to allow sliding with minimal friction.

The blade 11 shape of this prosthesis is oval with its major axis vertical. Its surface 12 is usually planar but may be slightly convex to match the concavity of the blade 1 of the corresponding superior articular process 3. It is directed forward and outward to match with the surface 2 of the blade 1 of the superior articular process 3 of the inferior vertebra. Its sizes correspond to that replaced articular surface and even may be reduced by 1 or 2 mm in the front to increase frontal posterior diameter of foramen and therefore prevent any nerve root compressions.

Similarly to the blade 1 of the superior articular process 3 prosthesis, this prosthetic blade 11 of the inferior articular prosthesis 13 bears in contact against the remaining bone of the articular prosthesis 13 or replaces entirely this articular process 13. Its bony face 14 and its articular surface 12 are comparable with that of the blade 1 of the superior articular process 3 prosthesis, fitted to the anatomy of the considered vertebra.

In the event the fragility of the remaining bone justifies the total replacement of inferior articular process 13, the blade 11 of the prosthesis mimics the anatomical shape of this inferior articular process 13: its articular surface 12 stays the same as that used for partial replacement when the opposite face is made with full material effecting one convex smooth face which is the lateral and posterior limit of the spinal canal and posterior limit of the foramen.

The blade 11 of the inferior articular process prosthesis joins with anchoring means by widening in sessile base 16 which is superior and makes a lateral rolling motion around the bony base of inferior articular process 13 which has a posterior and medial position in relation to blade 11 of the inferior articular process 13 prosthesis.

Advantageously, in the event two prosthetic blades (one superior 1 and the other inferior 2) are needed on one same vertebra, they make one "solid cast" with the common anchoring vertebral support 7: this resulting to increase their stability since they use the same anchoring means.

When the prosthetic blade 11 of the inferior articular process 13 is implanted on the most superior vertebra of the selected assembly, it is fitted in isolated way on this vertebra and therefore is supported by its sessile base 16 on its support 7 which provides it with a vertebral anchorage onto at least one of three points which are transverse process 8, spinous process 9 and pedicle 10.

Advantageously, the posterior vertebral articular prosthetic blades 1 and 11 may be implanted in an isolated way or connected with one vertebral internal dynamic orthosis and/or with one or many intervertebral disc prostheses which will reduce the strength applied to these articular prostheses.

The anchoring means of the prosthetic blades 1 and 11 have some supports 7 and some anchoring means onto at least one different part of each vertebra. Thus, each support plate 7 of the anchoring means extends facing vertebral pedicle 10 and may be anchored to the vertebra on at least one pedicle 10 by one intrapedicular screw 17 with a milled head fitted into one corresponding perforation 18 in the plate 7. According to the estimated neurological risks, the intrapedicular screw 17 may be shorter, always directed toward pedicle 10 but limited in depth to the posterior arch cortex and to the cancellous underlying bone facing the pedicle 10, without penetration into the latter to prevent any protrusion in the spinal canal or foramen.

Each anchoring means plate 7 also advantageously extends facing the lateral faces of the spinous process, on each side, and likewise has means for anchoring onto this spinous process 9. In order to accomplish this, the end 19 of the plate lying opposite the spinous process 9 has one bulge 20 projecting in the frontal plane and in the horizontal direction so as to form a shoulder for retaining an encircling arrangement which may be constituted by a self-locking collar 21 made of metal or synthetic material or one flange 22 surrounding the spinous process 9 and clamping the end 19 of the plate. The flange 22 may be constituted by one frame surrounding the spinous process 9 and the end 19 of the plate, and by one screw 24 which has a vertical axis and is fitted through a vertical threaded hole in the frame, and the free end of which is provided with a shoe 25 which is supported on the upper face of the spinous process 9. Thus the frame is locked with respect to the spinous process 9. The flange 22 likewise has one screw 26 with a frontal horizontal axis which is fitted into a horizontal threaded hole in the frame and the free end of which is provided with one shoe 27 which is supported on the end 19 of the plate in order to clamp it laterally and horizontally against the spinous process 9. After the screw 26 has been tightened, the retaining shoulder formed by the bulge locks the flange 22 in horizontal translation with respect to the free end 19 of the plate, the shoe 27 coming up against the said bulge. The flange 22 links together the two plates 7 and thus constitutes common means for anchoring the said two plates 7 to the spinous process 9 of the vertebra.

Likewise, each plate 7 of the anchoring devices advantageously extends facing at least one transverse process 8 of the vertebra, and has means for anchoring onto a transverse process 8. The said anchoring means may be formed by at least one hook 28 (left-hand plate in FIG. 6) which is articulated, at the transverse end 29 of the plate 7, about a horizontal axis 30 and is supported on the upper face and/or on the lower face of the transverse process 8. The transverse end 29 of the plate 7 therefore has, for each hook 28, a yoke 31 in which the hook 28 is articulated about its spindle 30. Each hook 28 is provided, at its opposite end to the tranverse process 8, with a vertical screw 32 which is fitted into a threaded hole in the hook 28 and is supported on a horizontal surface of the bottom of the yoke 31 of the plate 7 in order to clamp the said hook 28 against the corresponding surface of the transverse process 8.

Figure 6:
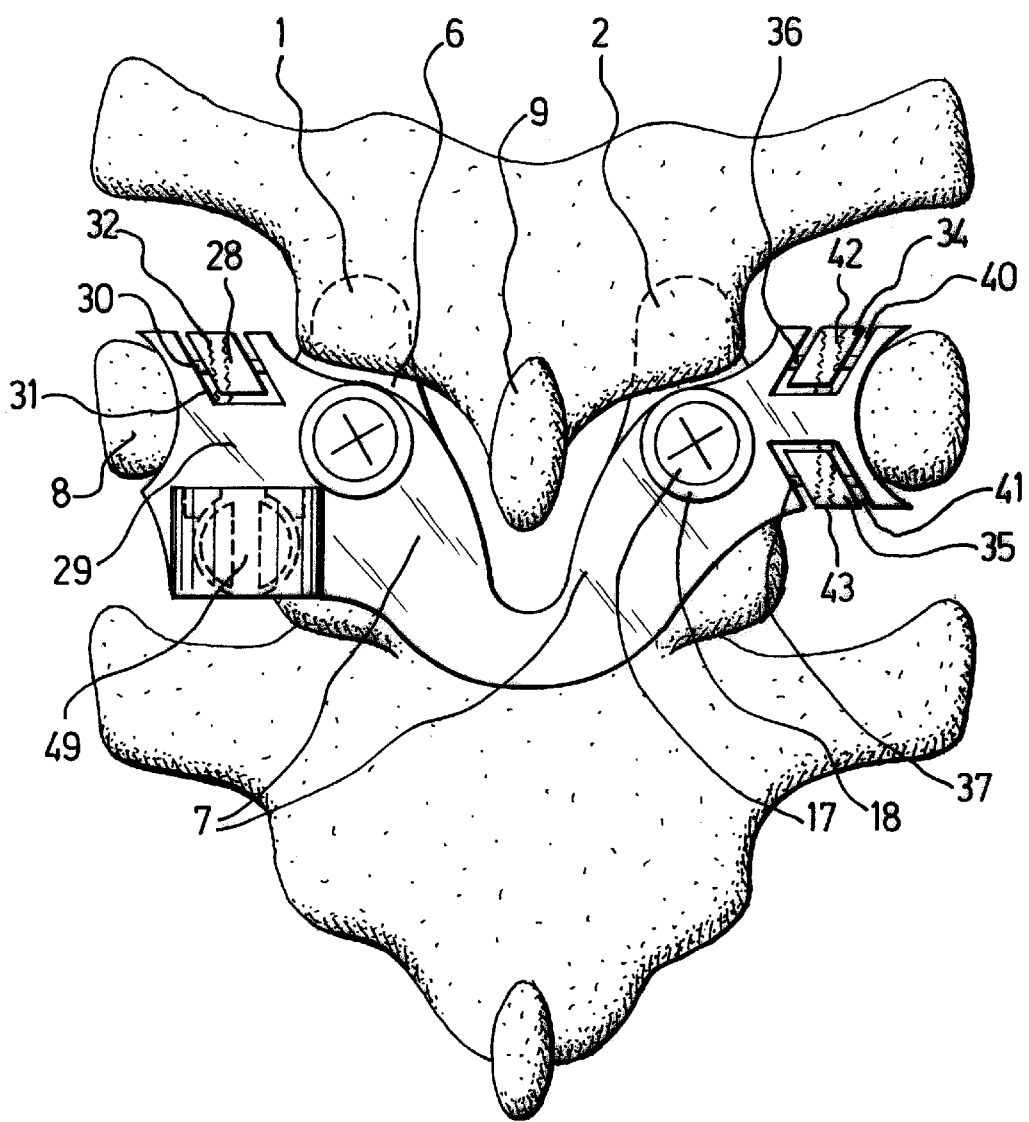
FIG. 6 is a diagrammatic rear view of another embodiment into which the vertebra has no spinous process: the plate is of a cast solid type and bridges between two paraspinal grooves posteriorly covering and protecting the spinal canal.

In FIG. 6, the means for anchoring the right-hand plate 7 has a clamping claw formed by two hooks 34 and 35 which are articulated, with respect to the plate 7, about two horizontal parallel spindles 36 and 37. In a variant, the anchorage onto the transverse process 8 may be brought about by a self-locking clamping collar 39 (similar to the one 21 used on the spinous process 9) made of metal or synthetic material. Each hook 34 and 35 is similar to the above described hook 28 and is mounted in a yoke 40 and 41 of the plate 7 with a vertical clamping screw 42 and 43 which is supported on a horizontal surface of the bottom of the yoke 40 and 41 in order to clamp the said hook 34 and 35 against the corresponding surface, the upper surface and the lower surface, respectively, of the transverse process 8. The respective free ends of the two hooks extend facing one another in an opposed manner and are clamped towards one another under the effect of the screws 42 and 43 in order to imprison the transverse process 8. Instead of the two screws 42 and 43 it is possible to provide a tightener having two reversed screws threads, which links the two hooks 34 and 35 to one another and is accessible from the top or bottom in order to clamp or unclamp the two hooks 34 and 35. A claw of this kind may also be provided for the left-hand plate 7.

FIG. 6 represents a variant form of embodiment in which the plate 7 extends in the two paravertebral grooves, the vertebra not having any spinous process. The plate 7 is anchored onto the two transverse process 8 and into the pedicles 10. The plate forms a bridge covering the posterior vertebral arch and protecting the spinal canal.

Figure 4:
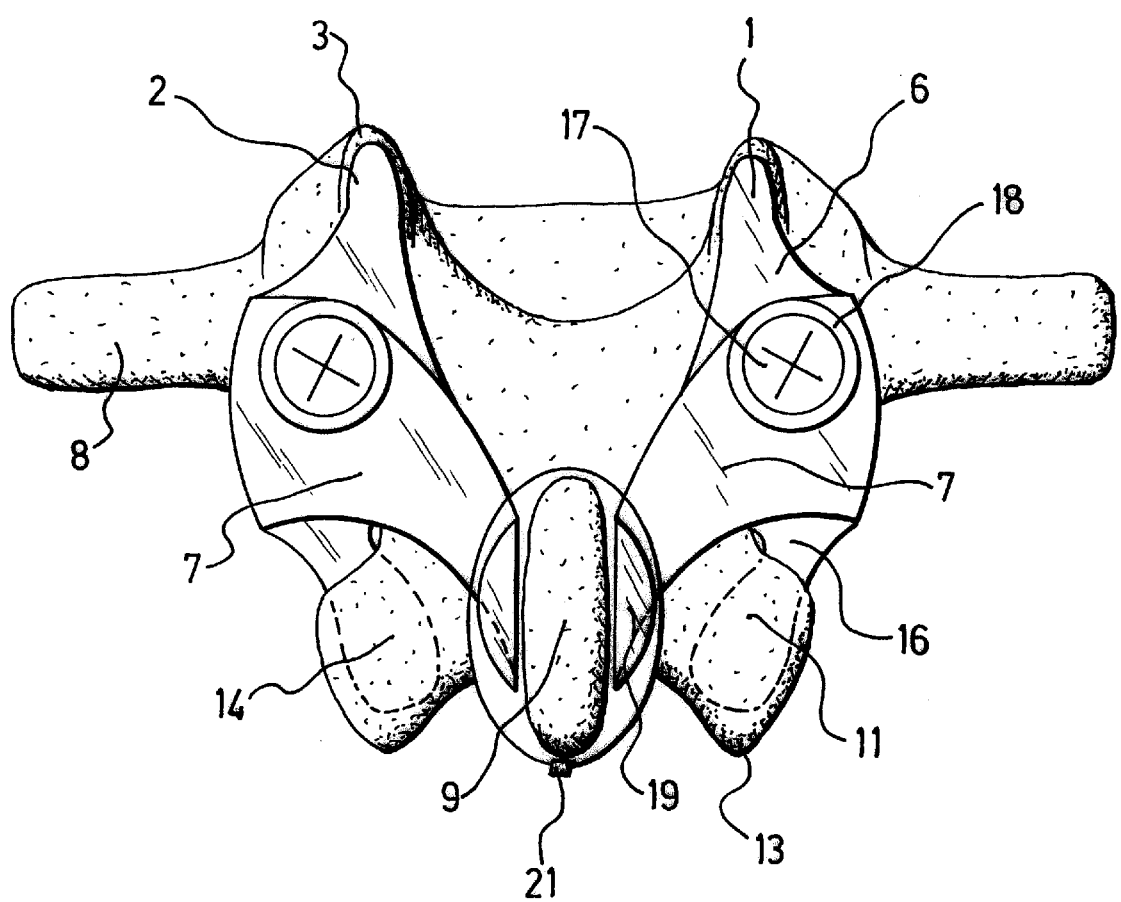
FIG. 4 is a diagrammatic rear view of one vertebral implanted prosthesis anchored onto the vertebra by two points into the pedicles and onto the spinous process.

FIG. 4 represents another variant in which the plates 7 are anchored solely by the intrapedicular screws 17 and by the flange 22 onto the spinous process 9.

Figure 5:
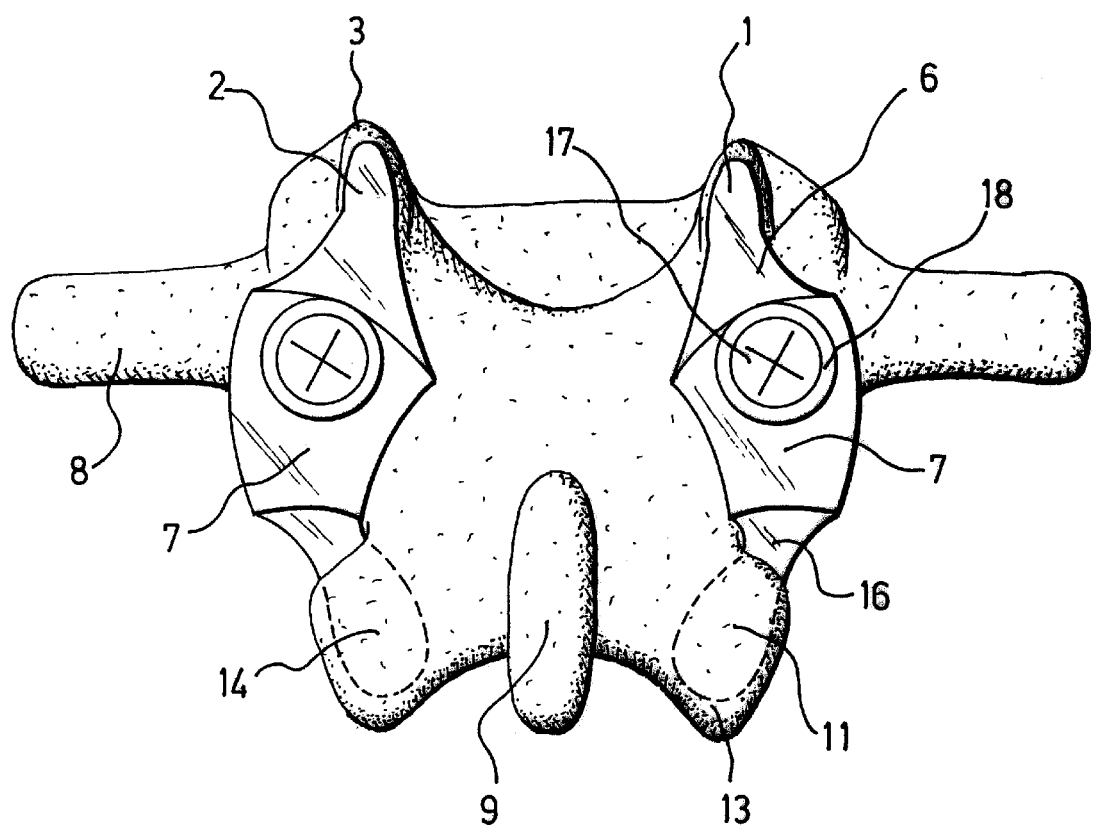
FIG. 5 is a diagrammatic rear view of one vertebral implanted prosthesis anchored onto the vertebra by one only intrapedicular screw on each side of the spinous process.

FIG. 5 represents another variant in which the plates 7 are anchored solely by the intrapedicular screws.

Figure 7:
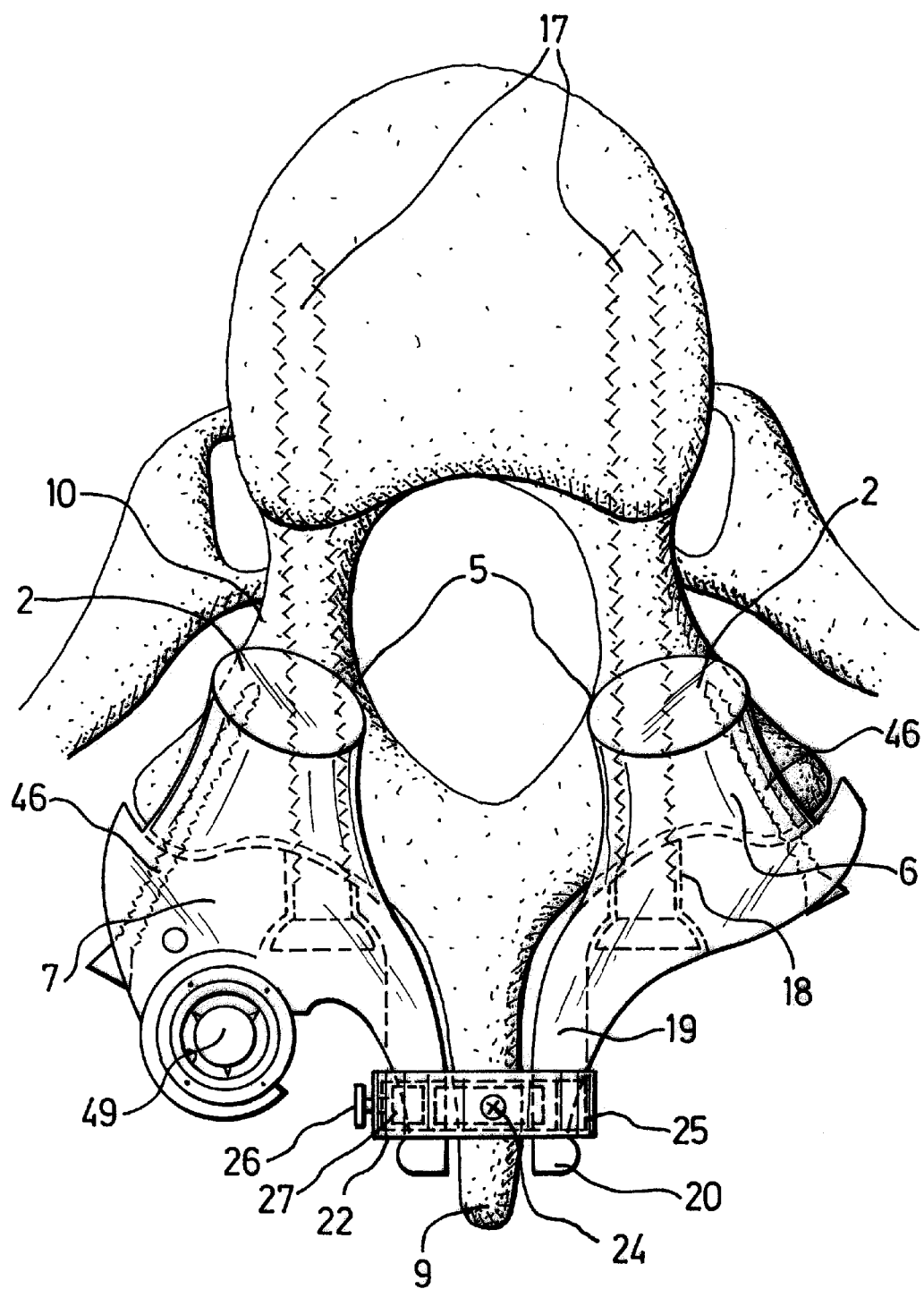
FIG. 7 is a diagrammatic superior view of an implanted vertebral prosthesis at the level of the $12^{th}$ thoracic vertebra which has no transverse processes: one oblique screw is directed towards pedicle and stabilizes the prosthesis.

FIG. 7 represents another form of embodiment which is more specifically intended for the thoracic vertebra T12 which, generally speaking, have no transverse processes. Each plate 7 nevertheless fits the shape of the stump of the transverse process 8, to which stump it is fixed by an oblique screw 46 oriented in the direction of the pedicle 10. The plates 7 are also fixed by intrapedicular screws 17 and a clamping flange 22 onto the spinous process 9.

Figure 8:
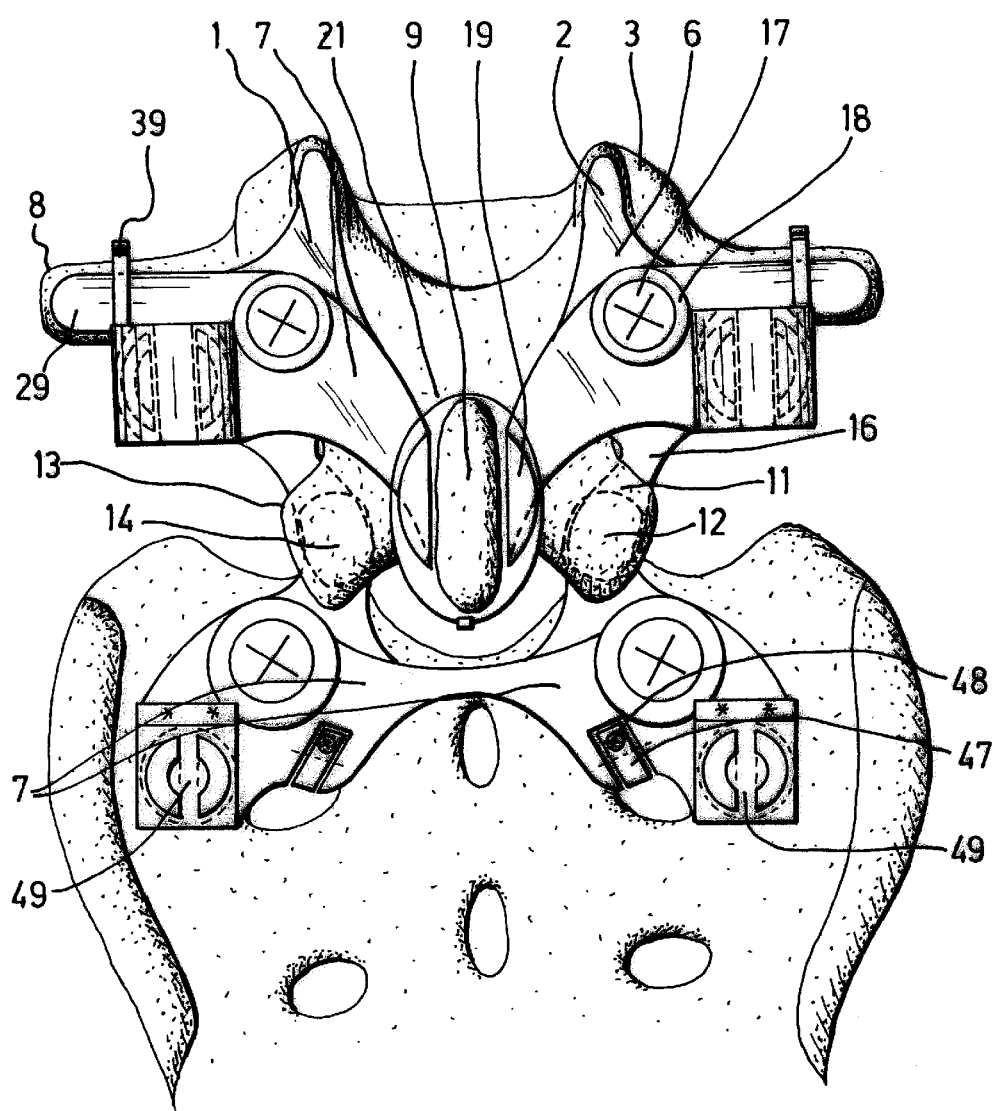
FIG. 8 is a diagrammatic posterior view of the implanted prosthesis at the $1^{st}$ sacral vertebra level with a cast solid plate anchored onto the pedicles and the $1^{st}$ sacral holes.

FIG. 8 represents the case of the sacral vertebra S1 which has no transverse process but a sacral ala; use is made of a continuous plate 7 extending on both sides of the hypotrophic spinous process 9 while forming a bridge above this spinous process 9. The plate 7 may be anchored by two lower hooks 47 which are similar to the above-described hooks 28 of the transverse processes and are supported on the upper edges of the two first sacral holes. Each hook 47 is clamped by a clamping screw 48 which is fitted into a threaded hole in the hook 47 and is supported on a vertical face of the plate 7. The plate 7 is fixed onto vertebra Si by two intrapedicular screws 17 which pass through the orifice 18 provided in the plate and are directed within the vertebral body of S1, towards its upper vertebral plateau. Two other screws (not represented) may stabilize the plate by fixing it laterally to the sacral ala.

The surgical procedure for fitting these prostheses is that used for conventional posterior spinal surgery with opening the two paravertebral muscular grooves while keeping intact the intervertebral ligament system.

The joints are opened by taking off the articular capsules and then the remaining bone and cartilaginous surfaces of vertebral facets. The fringing osteophytes are taken out mostly to increase space in front for foramen and medially for the spinal canal and therefore to negate any nerve root compressions as in the event of lumbar spinal stenosis. In case after the required resection of bone for implanting prosthesis the articular process stump is too weak, it is better to effect its removal and then to insert one total articular process prosthesis.

The vertebral facet prosthesis, total or only joint, is then selected according to the treated level, and fitted; its sizes and its direction are checked for well matching with that will be opposite to it.

The anchorage is made in accordance to the faced anatomical shapes, according to various combinations with the three anchoring points which are spinous process, transverse processes and pedicles. According to the estimated neurological risks, the "intrapedicular" screw may be very short, limited to the posterior cortex and to the cancellous underlying bone, facing pedicle without penetration into it, in order to prevent any protrusion in the spinal canal or foramen: it joins then as often as not to an anchorage onto the transverse and/or spinous processes in order to insure the stability of the assembly.

The procedure ends by closing the surgical wound, or may be extended with embodiment of spinal dynamic device in order to reduce the strength sustained by these joint facets prostheses and other paravertebral elements. Eventually, according to the particular cases, the intervertebral discs may have a replacement by intervertebral disc prostheses which will reduce the strength applied anteriorly to the spine (and therefore partially to posterior joint facets) while preserving the greatest possible mobility.

I claim:

1. A prosthetic support element for a vertebral articular process for preserving the spinal stability and the potential of functional motion without damaging the spinal muscle-ligament system, comprising:

at least one posterior support plate for rigid anchorage to a vertebra and extending against at least one portion of a posterior arch of the vertebra, at least one prosthetic blade carried by said support plate and extending from said support plate, said prosthetic blade including an artificial articular surface having a shape, position and orientation corresponding to the shape, position and orientation of a natural articular facet replaced by said articular surface, wherein said element has stiff anchoring means for anchoring said support plate on a transverse process and including a hook, a claw, or a clamping collar for the support plate facing said transverse process.

2. A prosthetic element as in claim 1, wherein said prosthetic blade bears a flat or concave superior artificial articular surface for replacing an inferior joint facet and then directed toward the corresponding superior joint facet of the inferior vertebra.

3. A prosthetic element as in claim 1, wherein said prosthetic blade bears a flat or concave inferior artificial articular surface for replacing an inferior joint facet and then directed toward the corresponding superior joint facet of the inferior vertebra.

4. A prosthetic element as in claim 1, wherein said at least one prosthetic blade (1, 11) is fitted to bear in contact against a residual part of an articular process, said prosthetic blade having a face opposite to the articular surface (2, 12) facing a residual part of corresponding articular process (3, 13).

5. A prosthetic element as in claim 1, wherein said at least one prosthetic blade has a tuberous shape with an artificial articular surface (2, 12), and a bowed bump to posteriorly and laterally position the spinal canal and posteriorly position the foramen as made by the natural articular process.

6. A prosthetic element as in claim 1, wherein said element has a plurality of said prosthetic blades (1, 11, 5,) linked to one support plate (7) and a sessile base (6, 16), said entire prosthetic element being made from a single piece of stiff biocompatible material.

7. A prosthetic element as in claim 1, wherein each support plate (7) includes a convex face adapted to fit and to bear in contact against the concave surface of a posterior vertebral arch, and wherein each support plate (7) comprises a plate so constructed as to prevent problems with the adjacent natural soft tissues.

8. A prosthetic element as in claim 1, wherein said element has one support plate on each side of spinous process (9), said anchorage means of the support plate (7) being fitted to anchor said support plate (7) against the posterior arch of the vertebra:

in connection with the pedicle (10) of the facing posterior arch, or in connection with the pedicle (10) and on a vertebral transverse process (8) or spinous process (9), or on a vertebral transverse process (8) and on the spinous process (9), or on a transverse process (8) on the spinous process (9), and in connection with the pedicle (10).

9. A prosthetic element as in claim 1, wherein said element has one support plate (7) extending on only one side of vertebral spinous process (9).

10. A prosthetic element as in claim 1, wherein said element has one bilateral support plate (7) extending on both sides of vertebral spinous process (9).

11. A prosthetic element as in claim 1, wherein said element has two support plates (7), one on each side of vertebral spinous process (9).

12. A prosthetic element as in claim 1, wherein said element has two support plates (7) which extend facing the spinous process (9) and anchor against the posterior arch of the vertebra by common anchorage means (21, 22).

13. A prosthetic element as in claim 1, wherein said anchoring means has at least one hook articulated on the support plate about a spindle, said hook carrying a clamping screw fitted into a threaded hole in said hook, said screw being supported either directly or indirectly on said support plate, so as to cause said hook to pivot about said spindle.

14. A prosthetic element as in claim 13, wherein said anchoring means has at least one clamping claw formed by two hooks, having mutually facing free ends clamped towards one another.

15. A prosthetic element as in claim 1, including means for stiff anchoring of one support plate onto a spinous process and at least one collar or flange for clamping said support plate facing said spinous process.

16. A prosthetic element as in claim 1, wherein each support plate carries means for coupling one spinal instrumentation.

17. A prosthetic element as in claim 1, wherein each support surface of each prosthetic blade and each support plate is formed of porous metal having scattered points thereon.

18. A prosthetic element as in claim 1, wherein each bony support surface of each prosthetic blade or support plate is coated with a layer of hydroxy-apatite.

19. A vertebral articular prosthesis having a superior prosthetic element comprising at least one inferior prosthetic blade carried by and extending from a posterior support plate adapted to extend against at least one portion of a posterior arch of the superior vertebra of the joint to be fitted for rigid anchorage to said superior vertebra, said inferior prosthetic blade including an artificial articular surface having a shape, position and orientation corresponding to the shape, position and orientation of a natural articular facet a superior vertebra replaced by said articular surface, an inferior prosthetic element comprising at least one superior prosthetic blade carried by and extending from a posterior support plate adapted to extend against at least one portion of a posterior arch of the inferior vertebra of the joint to be fitted for rigid anchorage to said inferior vertebra, said superior prosthetic blade including an artificial articular surface having a shape position and orientation corresponding to the shape, position and orientation of a natural articular facet of said inferior vertebra replaced by said artificial articular surface (2), said artificial articular surfaces having interconnected shapes fitted to effect a joint between two vertebrae.

* * * * *